(12) United States Patent
Kobayashi et al.

(10) Patent No.: US 10,520,455 B2
(45) Date of Patent: Dec. 31, 2019

(54) RESIDUAL STRESS MEASURING APPARATUS AND RESIDUAL STRESS MEASURING METHOD

(71) Applicant: SINTOKOGIO, LTD., Nagoya-shi, Aichi (JP)

(72) Inventors: Yuji Kobayashi, Toyokawa (JP); Akinori Matsui, Toyokawa (JP)

(73) Assignee: SINTOKOGIO, LTD., Nagoya-shi, Aichi (JP)

( * ) Notice: Subject to any disclaimer, the term of this patent is extended or adjusted under 35 U.S.C. 154(b) by 73 days.

(21) Appl. No.: 15/035,024

(22) PCT Filed: Nov. 30, 2015

(86) PCT No.: PCT/JP2015/083613
§ 371 (c)(1),
(2) Date: May 6, 2016

(87) PCT Pub. No.: WO2016/203672
PCT Pub. Date: Dec. 22, 2016

(65) Prior Publication Data
US 2017/0167988 A1    Jun. 15, 2017

(30) Foreign Application Priority Data

Jun. 18, 2015  (JP) ................................ 2015-123248

(51) Int. Cl.
*G01N 23/207* (2018.01)
(52) U.S. Cl.
CPC .................. *G01N 23/207* (2013.01)
(58) Field of Classification Search
CPC ............... G01N 23/203; G01N 23/207; G01N 2223/646
See application file for complete search history.

(56) References Cited

U.S. PATENT DOCUMENTS 3,402,291 A    9/1968  Weinman
3,868,506 A *  2/1975  Ogiso .................. G01N 23/207
                                                        378/72
(Continued)

FOREIGN PATENT DOCUMENTS

CN      1620602 A    5/2005
CN      201210151 Y  3/2009
(Continued)

OTHER PUBLICATIONS

Toshihiko Sasaki, "Overview of cos α method (plane stress measurement)," Inspection Engineering, ISSN 1342-9825, Jun. 1, 2015, vol. 20, No. 6, pp. 42-51, including partial English translation.
(Continued)

*Primary Examiner* — Dani Fox
*Assistant Examiner* — Soorena Kefayati
(74) *Attorney, Agent, or Firm* — Drinker Biddle & Reath LLP

(57) ABSTRACT

An apparatus includes an X-ray generating source; a first detecting element adapted to detect intensity of diffracted X-rays of the measuring object at a first detecting position; a second detecting element adapted to detect intensity of the diffracted X-rays of the measuring object at a second detecting position; a moving mechanism adapted to move each of the first detecting element and the second detecting element along a straight line extending in a direction orthogonal to a direction of incidence of the X-rays; a movement control unit adapted to control respective detecting positions of the first detecting element and the second detecting element by driving the moving mechanism; and a stress calculation unit adapted to calculate residual stress of the measuring object based on intensity peaks of the diffracted X-rays detected, respectively, by the first detecting element and the second detecting element each moved by the moving mechanism.

16 Claims, 5 Drawing Sheets

(56) References Cited

U.S. PATENT DOCUMENTS

| | | | |
|---|---|---|---|
| 4,125,771 A | 11/1978 | Erwin | |
| 4,426,718 A * | 1/1984 | Hayashi | G01N 23/207 378/72 |
| 4,489,425 A * | 12/1984 | Borgonovi | G01N 23/207 378/72 |
| 4,561,062 A * | 12/1985 | Mitchell | G01N 23/207 378/72 |
| 4,686,631 A * | 8/1987 | Ruud | G01N 23/207 378/72 |
| 5,125,016 A * | 6/1992 | Korhonen | G01N 23/207 250/370.1 |
| 5,148,458 A * | 9/1992 | Ruud | G01L 1/25 378/70 |
| 5,155,751 A * | 10/1992 | Chohata | C23C 2/28 378/70 |
| 5,414,747 A * | 5/1995 | Ruud | G01N 23/207 378/72 |
| 5,848,122 A * | 12/1998 | Kurtz | G01N 23/20033 378/80 |
| 5,966,423 A * | 10/1999 | Quinn | G01N 23/20025 378/79 |
| 6,353,656 B1 * | 3/2002 | LeVert | G01N 23/20 378/70 |
| 6,424,695 B1 * | 7/2002 | Grodzins | G01N 23/04 378/70 |
| 7,646,847 B2 * | 1/2010 | He | G01N 23/207 378/71 |
| 8,848,871 B2 * | 9/2014 | Chapman | G01N 23/203 378/87 |
| 9,031,188 B2 * | 5/2015 | Belcher | G01N 23/203 378/58 |
| 9,535,019 B1 * | 1/2017 | Rothschild | G01N 23/203 |
| 2011/0305318 A1 * | 12/2011 | Robinson | G01N 23/087 378/88 |
| 2015/0146857 A1 * | 5/2015 | Fujita | G01N 23/20 378/72 |
| 2016/0356692 A1 * | 12/2016 | Ye | G01N 21/49 |

FOREIGN PATENT DOCUMENTS

| | | |
|---|---|---|
| CN | 102435623 A | 5/2012 |
| CN | 104048978 A | 9/2014 |
| CN | 104374499 A | 2/2015 |
| CN | 104634799 A | 5/2015 |
| JP | S53-003884 A | 1/1978 |
| JP | 2000-213999 A | 8/2000 |
| JP | 2001-056303 A | 2/2001 |
| JP | 2002-181638 A | 6/2002 |
| JP | 2002-333409 A | 11/2002 |
| JP | 2013-113734 A | 6/2013 |
| TW | 442656 B | 6/2001 |
| TW | 201221926 A | 6/2012 |
| TW | 201321731 A | 6/2013 |
| WO | WO 85/001342 | 3/1985 |

OTHER PUBLICATIONS

English-language translation of International Preliminary Report on Patentability (IPRP) dated Dec. 28, 2017 that issued in WO Patent Application No. PCT/JP2015/083613.

* cited by examiner (A)

(B)

RESIDUAL STRESS MEASURING APPARATUS AND RESIDUAL STRESS MEASURING METHOD

TECHNICAL FIELD

The present disclosure relates to a residual stress measuring apparatus and a residual stress measuring method.

BACKGROUND ART

An apparatus adapted to measure residual stress of a measuring object using X-rays is described in Patent Literature 1. The apparatus comprises an X-ray emitter adapted to emit X-rays to a measuring object, an imaging plate adapted to receive diffracted light from the measuring object, a rotating mechanism adapted to rotate the imaging plate, a laser device adapted to take a reading from the imaging plate, and a controller adapted to control these components.

The controller stores geometries of diffraction rings corresponding to residual stresses as references in advance. Then, the apparatus receives diffracted light from the measuring object using the imaging plate, acquires a diffraction ring by reading received light intensity with the laser device while rotating the imaging plate with the rotating mechanism, and compares the geometry of the acquired diffraction ring with the geometries of reference diffraction rings. Then, the apparatus calculates the residual stress corresponding to the diffraction ring of the closest geometry as the residual stress of the measuring object. When a measured diffraction ring is discontinuous, the apparatus calculates the residual stress by $\cos\alpha$ method based on the geometry of the diffraction ring.

CITATION LIST

Patent Literature

Patent Literature 1: Japanese Unexamined Patent Publication No. 2013-113734

SUMMARY OF INVENTION

Technical Problem

However, with the apparatus described in Patent Literature 1, there is a risk that the measurement of residual stress may take time. For example, since it is necessary to acquire signals by rotating the imaging plate, signal reading may take time. In the present technical field, it is desired to reduce the measurement time of residual stress.

Solution to Problem

A residual stress measuring apparatus according to one aspect of the present invention comprises: an X-ray generating source adapted to radiate X-rays toward a measuring object; a first detecting element adapted to detect intensity of diffracted X-rays of the measuring object at a first detecting position; a second detecting element adapted to detect intensity of the diffracted X-rays of the measuring object at a second detecting position different from the first detecting position; a moving mechanism adapted to move each of the first detecting element and the second detecting element along a straight line extending in a direction orthogonal to a direction of incidence of the X-rays; a movement control unit adapted to control respective detecting positions of the first detecting element and the second detecting element by driving the moving mechanism; and a stress calculation unit adapted to calculate residual stress of the measuring object based on intensity peaks of the diffracted X-rays detected, respectively, by the first detecting element and the second detecting element each moved by the moving mechanism.

The apparatus comprises the first detecting element adapted to detect the intensity of diffracted X-rays of a measuring object at a first detecting position and the second detecting element adapted to detect the intensity of the diffracted X-rays of the measuring object at a second detecting position different from the first detecting position, using the moving mechanism and the movement control unit. With this configuration, diffracted X-rays can be obtained at two angles by a single X-ray irradiation. Furthermore, by moving, respectively, along straight lines extending in directions orthogonal to a direction of incidence of the X-rays, the first detecting element and the second detecting element can acquire respective X-ray intensity distributions for each element (diffraction peaks). Also, because the residual stress of a measuring object can be calculated by acquiring at least two diffraction peaks, the need to acquire all data on a diffraction ring by rotating the imaging plate is eliminated. Thus, compared to conventional residual stress measuring apparatus, measurement time of residual stress can be reduced.

According to one embodiment, the movement control unit may synchronize movement of the first detecting element and movement of the second detecting element with each other. In this case, compared to when the first detecting element and the second detecting element are controlled individually, the measurement time of residual stress can be reduced.

A residual stress measuring method according to another aspect of the present invention is a residual stress measuring method for measuring residual stress of a measuring object using a residual stress measuring apparatus equipped with an X-ray generating source, a first detecting element adapted to detect intensity of diffracted X-rays of the measuring object at a first detecting position, a second detecting element adapted to detect intensity of the diffracted X-rays of the measuring object at a second detecting position different from the first detecting position, and a moving mechanism adapted to move each of the first detecting element and the second detecting element along a straight line extending in a direction orthogonal to a direction of incidence of the X-rays, the residual stress measuring method comprising: an X-ray irradiation step of radiating X-rays toward the measuring object; a movement control step of moving the first detecting element and the second detecting element by driving the moving mechanism; and a stress calculation step of calculating residual stress of the measuring object based on intensity peaks of the diffracted X-rays of the measuring object detected, respectively, by the first detecting element and the second detecting element during execution of the movement control step.

According to one embodiment, movement of the first detecting element and movement of the second detecting element may be synchronized with each other in the movement control step.

The residual stress measuring method described above provides advantageous effects similar to those of the residual stress measuring apparatus described above.

Advantageous Effects of Invention

According to aspects and embodiments of the present invention, the measurement time of residual stress can be reduced.

DESCRIPTION OF EMBODIMENTS

The present embodiment will be described below with reference to the drawings. Note that in the following description, same or equivalent elements are denoted by the same reference signs and redundant description thereof will be omitted.

A residual stress measuring apparatus 1 according to the present embodiment is an apparatus adapted to measure residual stress of a measuring object using X-rays. The residual stress measuring apparatus 1 can be adopted, for example, on a factory line to check quality of manufactured products, but this is not restrictive. The measuring object, for example, is non-orientated (isotropic crystalline structure), and can be formed of a polycrystalline metallic material.

Figure 1:
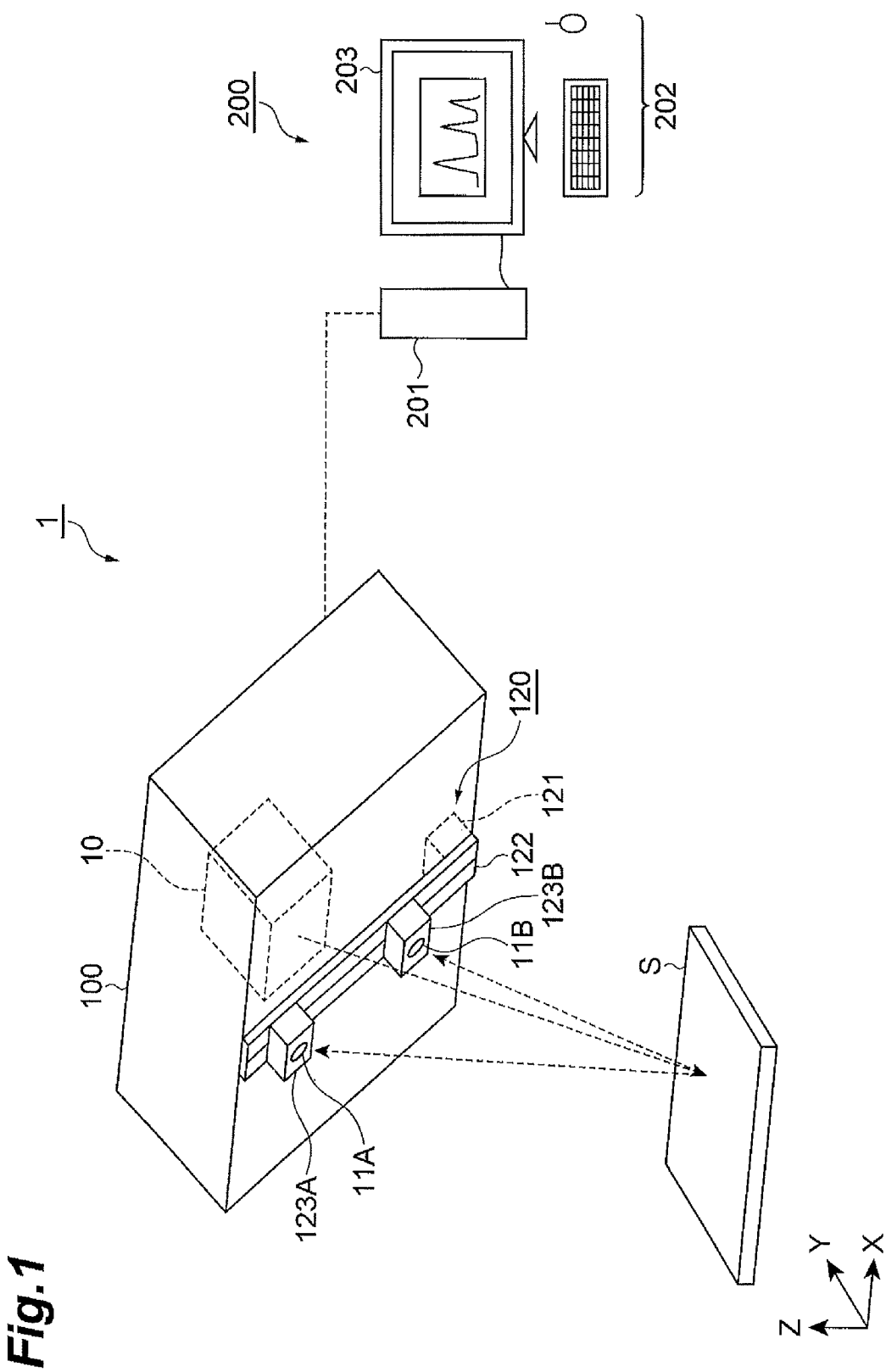
FIG. 1 is a schematic diagram describing a configuration of a residual stress measuring apparatus according to the present embodiment.

FIG. 1 is a schematic diagram describing a configuration of the residual stress measuring apparatus 1 according to the present embodiment. As shown in FIG. 1, the residual stress measuring apparatus 1 is equipped with an apparatus body 100 including an X-ray generating source 10 as well as with a control apparatus 200.

The apparatus body 100 is a box-shaped casing which houses, for example, the X-ray generating source 10 therein. The X-ray generating source 10 is a device which comprises an X-ray tube and generates X-rays of a predetermined wavelength. The X-ray generating source 10 is fixed, for example, to the apparatus body 100. Regarding X-rays, X-rays of an appropriate wavelength are used according to a measuring object S. A window (an example of a collimator: not shown) for X-ray irradiation is formed in a front face of the apparatus body 100. The X-rays generated by the X-ray generating source 10 are radiated toward the measuring object S through the window.

The apparatus body 100 comprises a first detecting element 11A and a second detecting element 11B. Here, the first detecting element 11A and second detecting element 11B are placed on a side face of the apparatus body 100 in which the window (not shown) for X-ray irradiation is formed. The first detecting element 11A and second detecting element 11B detect respective intensities of the diffracted X-rays of the measuring object S. The first detecting element 11A is a zero-dimensional X-ray intensity measuring element. "Zero-dimensional" means that the X-ray intensity is measured at a placement location of the element. That is, the first detecting element 11A differs from a one-dimensional line sensor in which a plurality of elements are placed along a straight line and a two-dimensional imaging plate in which a plurality of elements are placed in a plane. The second detecting element 11B is also a zero-dimensional X-ray intensity measuring element. As the first detecting element 11A and second detecting element 11B, scintillation counters are used, for example.

The apparatus body 100 comprises a moving mechanism 120 adapted to move each of the first detecting element 11A and second detecting element 11B along a straight line extending in a direction orthogonal to a direction of incidence of the X-rays. The straight line extending in a direction orthogonal to a direction of incidence of the X-rays means a straight line on a plane with a normal vector coinciding with incident X-rays. In the example of FIG. 1, the moving mechanism 120 moves the first detecting element 11A and second detecting element 11B along a straight line extending in an X direction. As the moving mechanism 120, an electric actuator is used, for example. In a more specific example, the moving mechanism 120 comprises, for example, an electric motor 121, a ball screw portion 122, and nut portions 123A and 123B. The electric motor 121 is connected to a screw shaft of the ball screw portion 122 so as to give a turning force around an axial direction. The nut portions 123A and 123B are attached to the ball screw portion 122 in such a way as to be movable in the axial direction. The first detecting element 11A is attached to the nut portion 123A while the second detecting element 11B is attached to the nut portion 123B. When the electric motor 121 operates, the screw shaft of the ball screw portion 122 rotates, and the nut portions 123A and 123B move in the same direction in synchronization. That is, the first detecting element 11A and second detecting element 11B move in the same direction along the same screw shaft in synchronization. The first detecting element 11A and second detecting element 11B can change a detecting position of X-ray intensity on straight line using the moving mechanism 120.

The first detecting element 11A detects the intensity of the diffracted X-rays of the measuring object S at a first detecting position. The second detecting element 11B detects the intensity of the diffracted X-rays of the measuring object S at a second detecting position different from the first detecting position. The first detecting position and second detecting position can be varied according to material of the measuring object S and focal length. According to the present embodiment, the first detecting element 11A and second detecting element 11B move the same preset distance in synchronization. The preset distance is a distance within a range in which a necessary diffraction intensity distribution can be obtained.

The moving mechanism 120 is connected to the control apparatus 200. The control apparatus 200 is made up of a general-purpose computer which comprises a CPU (Central Processing Unit), a ROM (Read Only Memory), a RAM (Random Access Memory), a HDD (Hard Disk Drive), and the like. The control apparatus 200 comprises, for example, a processing unit 201, an input device 202, and an output device 203.

Figure 2:
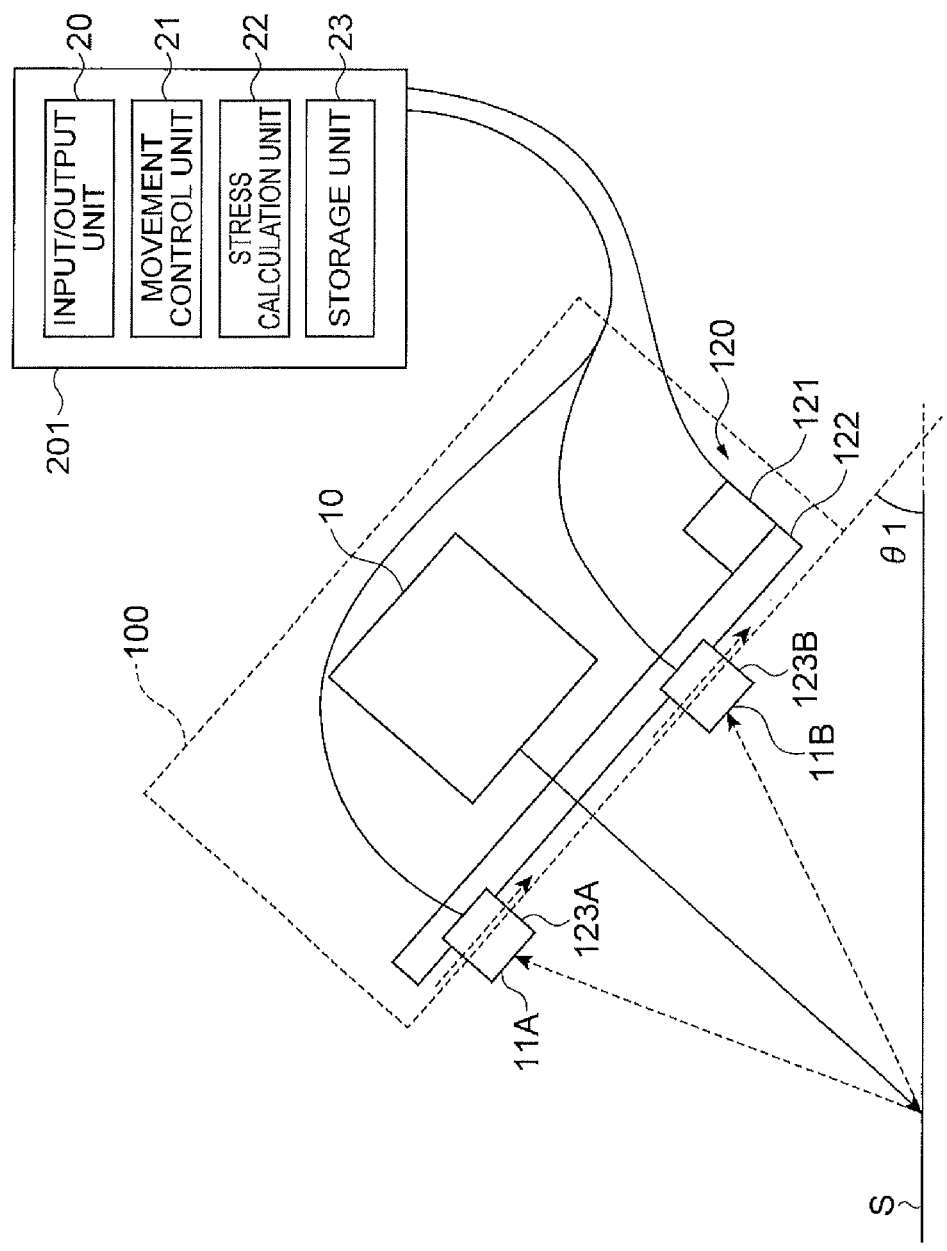
FIG. 2 is a diagram describing a schematic configuration of the residual stress measuring apparatus according to the present embodiment.

FIG. 2 is a diagram describing a schematic configuration of the residual stress measuring apparatus according to the present embodiment. As shown in FIG. 2, the processing unit 201 comprises an input/output unit 20, a movement control unit 21, a stress calculation unit 22, and a storage unit 23.

The input/output unit 20 includes communications equipment such as a network card and an input-output device such as a graphics card. For example, the input/output unit 20 is connected with the electric motor 121 in such a way as to be ready to communicate. The input/output unit 20 is connected, for example, with the input device 202 and output device 203 in such a way as to be ready to communicate. Furthermore, the input/output unit 20 is connected to the first detecting element 11A and second detecting element 11B. The movement control unit 21 and stress calculation unit 22 described below exchange information with each component via the input/output unit 20.

The movement control unit 21 controls the respective detecting positions of the first detecting element 11A and second detecting element 11B by driving the moving mechanism 120. For example, the movement control unit 21 preliminarily acquires a peak appearance angle determined based on material making up the measuring object S and controls the respective detecting positions of the first detecting element 11A and second detecting element 11B so as to include the peak appearance angle. The peak appearance position determined based on the material making up the measuring object S is stored, for example, in the storage unit 23.

Figure 3:
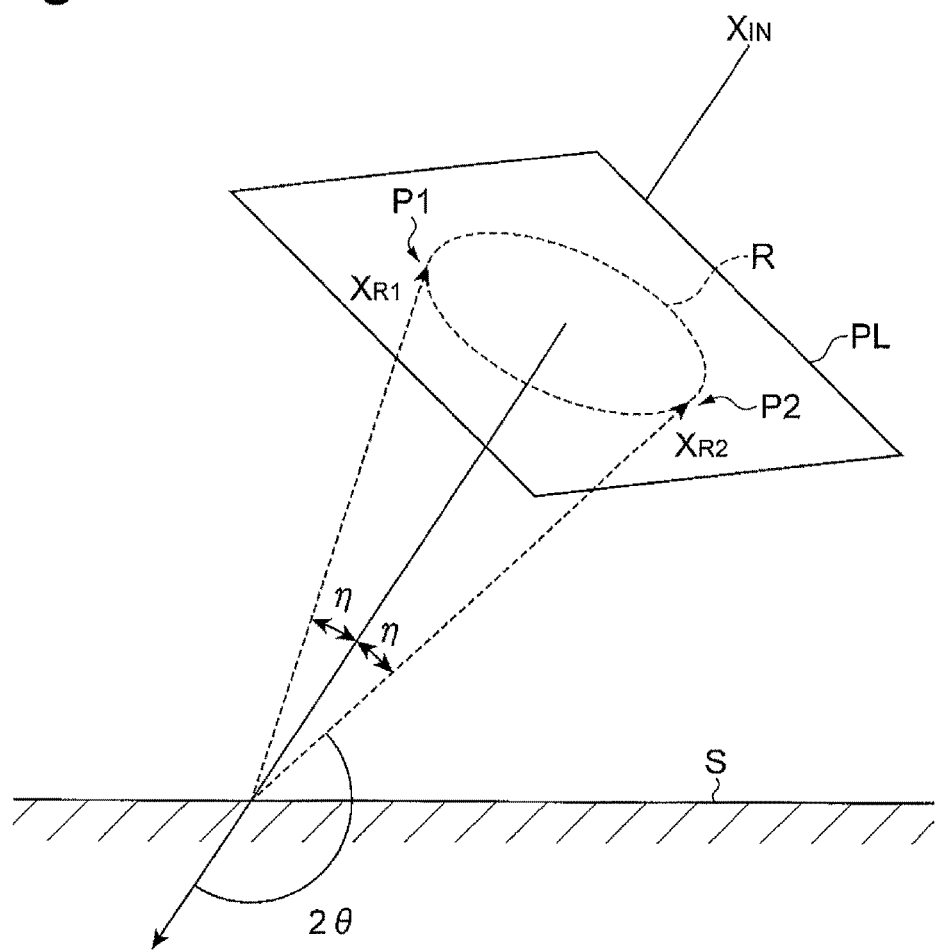
FIG. 3 is a schematic diagram describing a detecting position of the residual stress measuring apparatus according to the present embodiment.
Figure 4:
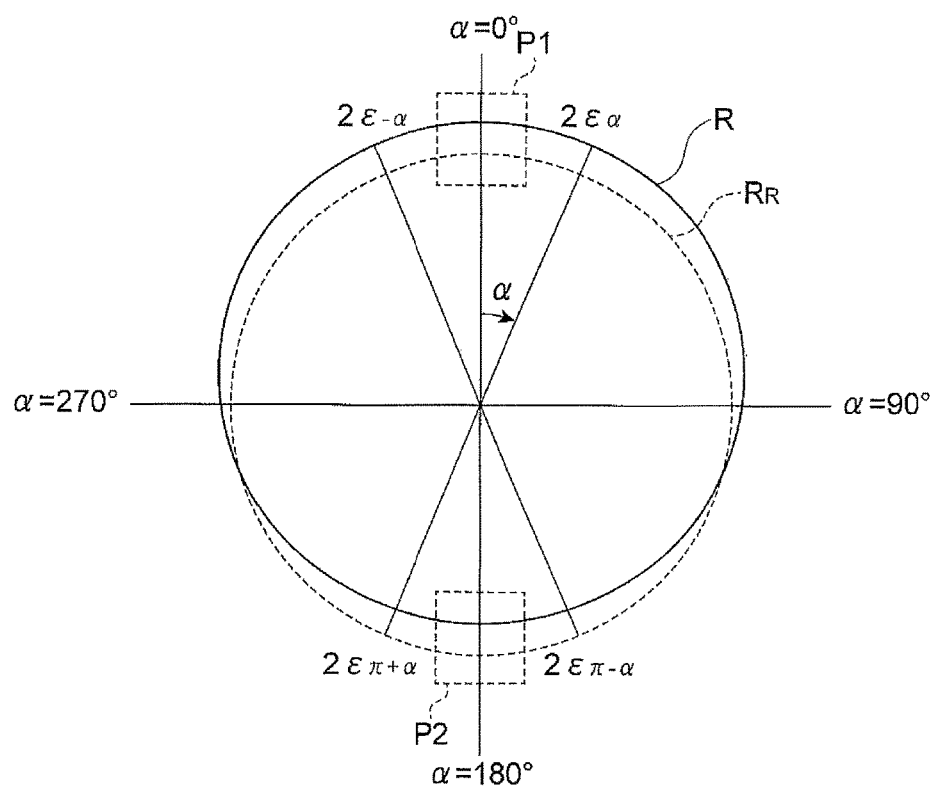
FIG. 4 is a schematic diagram describing a diffraction ring.

FIG. 3 is a schematic diagram describing a detecting position of the residual stress measuring apparatus 1 according to the present embodiment. FIG. 3 shows a case in which incident X-rays $X_{IN}$ are radiated toward the measuring object S and diffracted X-rays are outputted at a diffraction angle $2\theta$. In this case, a diffraction ring R is drawn by diffracted X-rays on a predetermined plane PL. Here, in the present embodiment, a case in which intensity peaks appear, respectively, at a detecting position corresponding to a 0-degree position on the diffraction ring of the diffracted X-rays and a detecting position corresponding to a 180-degree position on the diffraction ring of the diffracted X-rays and diffraction intensities are acquired in these portions (i.e., symmetrical points) is taken as an example. FIG. 4 is a schematic diagram describing a diffraction ring. In FIG. 4, parts corresponding to FIG. 3 are denoted by the same reference signs. As shown in FIGS. 3 and 4, diffracted X-rays $X_{R1}$ are detected at a first detecting position P1 corresponding to the 0-degree position on the diffraction ring and diffracted X-rays $X_{R2}$ are detected at a second detecting position P2 corresponding to the 180-degree position on the diffraction ring R. In this case, the movement control unit 21 sets such that the first detecting element 11A will move in a range including the first detecting position PI corresponding to the 0-degree position on the diffraction ring R. Likewise, the movement control unit 21 sets such that the second detecting element 11B will move in a range including the second detecting position P2 corresponding to the 180-degree position on the diffraction ring R. Consequently, diffracted X-rays at two angles are obtained by a single X-ray irradiation, and two X-ray diffraction intensity distributions can be obtained.

The stress calculation unit 22 acquire diffraction peaks based on the X-ray diffraction intensity distributions (angle-intensity relationships) detected, respectively, at the first detecting position P1 and second detecting position P2. Here, two intensity peaks, an intensity peak corresponding to the 0-degree position on the diffraction ring R and an intensity peak corresponding to the 180-degree position on the diffraction ring R, can be obtained. The diffraction ring $R_R$ of a broken line shown in FIG. 4 is a diffraction ring in the absence of residual stress in the measuring object. Compared to the diffraction ring $R_R$ in the absence of residual stress, a center location of the diffraction ring R in the presence of residual stress is displaced according to the residual stress. The stress calculation unit 22 calculates a residual stress value using this difference. For example, the stress calculation unit 22 calculates the residual stress value using a $\cos\alpha$ method. With the $\cos\alpha$ method, residual stress is obtained from a slope of a $\varepsilon$-$\cos\alpha$ chart which describes a relationship between $\cos\alpha$ ($\alpha$: central angle of diffraction) and distortion $\varepsilon$ expressed in terms of distortions at four locations ($\varepsilon_\alpha$, $\varepsilon_{\pi+\alpha}$, $\varepsilon_{-\alpha}$, $\varepsilon_{\pi-\alpha}$) on a diffraction ring. The stress calculation unit 22 calculates the slope (slope of a primary function) of the $\varepsilon$-$\cos\alpha$ chart using two points $\alpha=0°$, 180°. Then, the stress calculation unit 22 obtains the residual stress by multiplying the slope of the primary function by an X-ray stress measurement multiplier. The X-ray stress measurement multiplier is a constant determined by Young's modulus, Poisson's ratio, the complement of a Bragg angle, and an X-ray incidence angle and is stored beforehand, for example, in the storage unit 23. The stress calculation unit 22 may store the calculated residual stress in the storage unit 23 or output it to the output device 203.

Figure 5:
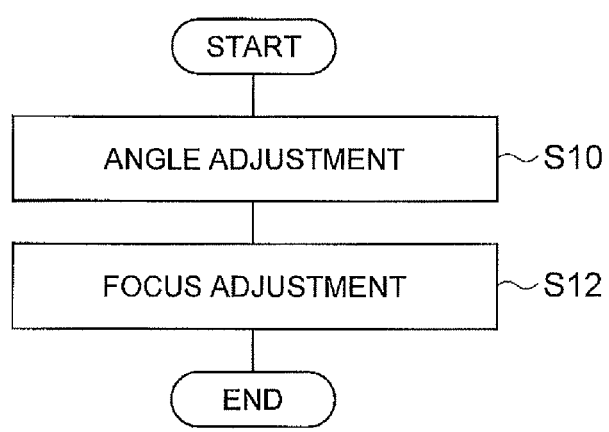
FIG. 5 is a flowchart showing a residual stress measuring method according to the present embodiment.
Figure 5:
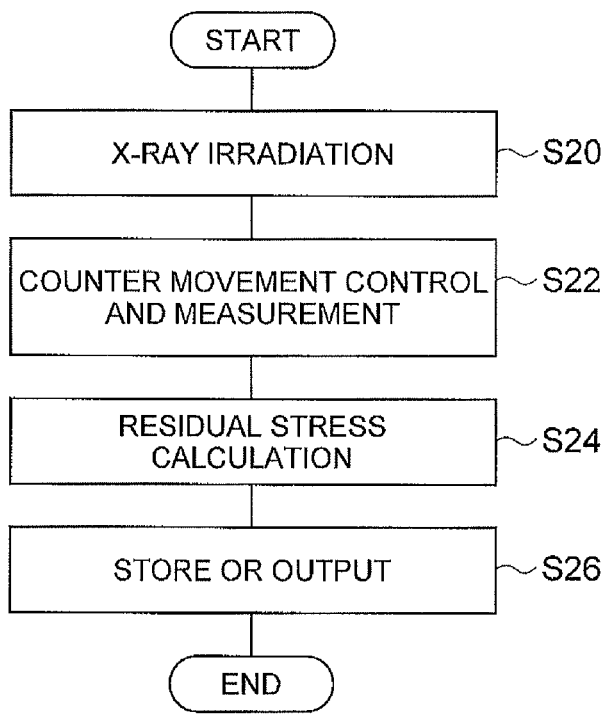

This concludes description of the configuration of the residual stress measuring apparatus 1. Next, a residual stress measuring method using the residual stress measuring apparatus 1 will be described. FIG. 5 is a flowchart showing the residual stress measuring method according to the present embodiment.

First, an adjustment process prior to residual stress measurement is performed. FIG. 5(A) is a flowchart showing the adjustment process prior to residual stress measurement. As shown in FIG. 5(A), an angle adjustment process (S10) is carried out first. In this process, an angle of incident X-rays with respect to the measuring object S is adjusted. For example, as shown in FIG. 2, by adjusting a tilt angle $\theta1$ by tilting the apparatus body 100, the angle of the incident X-rays is adjusted. Note that the process of tilting the apparatus body 100 may be performed by a separate device (control unit and actuator) or a measurer. The angle of incidence being measured is fixed at a predetermined angle (single angle) by the process of S10.

Next, a focus adjustment process (S12) is performed. In this process, focus of the incident X-rays with respect to the measuring object S is adjusted. For example, as height of the measuring object S is changed or position of the apparatus body 100 is changed, the focus of the incident X-rays is adjusted. Note that the process of changing the height or position may be performed by a separate device (control unit and actuator) or a measurer.

This ends the flowchart shown in FIG. 5(A). When the flowchart shown in FIG. 5(A) ends, conditions in which the residual stress of the measuring object S can be measured are established. Then, the residual stress is measured. FIG. 5(B) is a flowchart showing a method for measuring residual stress.

As shown in FIG. 5(B), an X-ray irradiation process (S20: X-ray irradiation step) is carried out first. In the X-ray irradiation process of S20, X-rays are radiated toward the measuring object S from the X-ray generating source 10. Next, during execution of the X-ray irradiation process of S20, a measurement process (S22: movement control step) is carried out. In the measurement process of S22, the first detecting element 11A and second detecting element 11B are moved by the moving mechanism 120 and movement control unit 21 and two X-ray diffraction intensity distributions are obtained based on detection results during the movement. When the measurement process of S22 finishes, the X-ray irradiation may be terminated. Next, a residual stress calculation process (S24: stress calculation step) is carried out. In the residual stress calculation process of S24, two intensity peaks are acquired by the stress calculation unit 22 based on the two X-ray diffraction intensity distributions obtained during the movement. Then, by the stress calculation unit 22, the slope of the ε-cosα chart is calculated and multiplied by an X-ray stress measurement multiplier, and the residual stress is calculated. Finally, the residual stress calculated by the stress calculation unit 22 is stored in the storage unit 23 or outputted to the output device 203.

This concludes the flowchart shown in FIG. 5(B). By performing the control process shown in FIG. 5(B), it is possible to calculate the residual stress using the data obtained by moving the first detecting element and second detecting element.

As described above, the residual stress measuring apparatus 1 according to the present embodiment comprises the first detecting element 11A adapted to detect the intensity of diffracted X-rays at the first detecting position P1 and the second detecting element adapted to detect the intensity of diffracted X-rays at the second detecting position P2 different from the first detecting position P1, by the moving mechanism 120 and movement control unit 21. With this configuration, diffracted X-rays can be obtained at two angles by a single X-ray irradiation (irradiation at one angle). Furthermore, by moving, respectively, along straight lines extending in directions orthogonal to a direction of incidence of the X-rays, the first detecting element 11A and the second detecting element 11B can acquire respective X-ray intensity distributions for each element (diffraction peaks). Also, because the residual stress of the measuring object S can be calculated by acquiring at least two diffraction peaks, the need to acquire all data on a diffraction ring by rotating the imaging plate is eliminated. Thus, compared to conventional residual stress measuring apparatus, the measurement time of residual stress can be reduced.

Also, with the residual stress measuring apparatus 1 according to the present embodiment, since there is no need to comprise a mechanism for rotating the imaging plate or a reading mechanism, the apparatus is simplified and reduced in weight in comparison with conventional residual stress measuring apparatus. Consequently, the apparatus becomes, easier to install or can be structured to be easier to incorporate into another machine than the conventional residual stress measuring apparatus. Furthermore, as the apparatus configuration is simplified, production cost of the apparatus can be reduced in comparison with conventional residual stress measuring apparatus.

Furthermore, as the movement control unit 21 synchronizes the movement of the first detecting element 11A and the movement of the second detecting element 11B with each other, the measurement time of residual stress can be reduced, compared to when the first detecting element 11A and second detecting element 11B are controlled individually.

An embodiment of the present invention has been described above, the present invention is not limited to the embodiment described above. The present invention can be embodied in various forms resulting from various changes or improvements made to the above-described embodiment based on the knowledge of those skilled in the art.

Whereas, for example, an example in which the residual stress measuring apparatus 1 is adopted on a factory line has been described in the above embodiment, the residual stress measuring apparatus 1 may be installed on an apparatus not placed on a line. Also, an example in which the residual stress measuring apparatus 1 comprises the first detecting element 11A and the second detecting element 11B has been described in the above embodiment, it is sufficient if the residual stress measuring apparatus 1 comprises at least two detecting elements. That is, the residual stress measuring apparatus 1 may comprise three or more detecting elements.

Also, whereas an example in which the moving mechanism 120 moves both the first detecting element 11A and second detecting element 11B using a set of the electric motor 121 and ball screw portion 122 has been described in the above embodiment, the first detecting element 11A and second detecting element 11B may be provided with respective electric motors and ball screw portions. In this case, the control apparatus 200 can control the movements of the first detecting element 11A and second detecting element 11B by controlling the respective electric motors of the first detecting element 11A and second detecting element 11B. By controlling two ball screw shafts, the control apparatus 200 can cause the first detecting element 11A and second detecting element 11B either to synchronize in synchronization or to move differently.

Furthermore, the residual stress measuring apparatus 1 according to the above embodiment may be incorporated into a shot peening apparatus or the like. In this case, the input/output unit 20 described in the above embodiment is configured to receive a signal outputted from a sequencer on a control board of the shot peening apparatus, and the measurement of residual stress is performed when the movement control unit 21 and stress calculation unit 22 operate based on the signal.

REFERENCE SIGNS LIST

1 . . . residual stress measuring apparatus, 2θ . . . diffraction angle, 10 . . . X-ray generating source, 11A . . . first detecting element, 11B . . . second detecting element, 21 . . . movement control unit, 22 . . . stress calculation unit, 120 . . . moving mechanism

The invention claimed is:
1. A residual stress measuring apparatus comprising:
an X-ray generating source adapted to radiate X-rays toward a measuring object;
a first detecting element adapted to detect an intensity of diffracted X-rays of the measuring object at a first detecting position;
a second detecting element adapted to detect an intensity of the diffracted X-rays of the measuring object at a second detecting position different from the first detecting position;
a moving mechanism adapted to move each of the first detecting element and the second detecting element along a straight line extending in a direction orthogonal to a direction of incidence of the X-rays, wherein the moving mechanism moves each of the first detecting element and the second detecting element such that a relative distance between the respective detecting positions of the first detecting element and the second detecting element and a position where the X-rays are irradiated changes;
a movement control unit adapted to control the respective detecting positions of the first detecting element and the second detecting element by driving the moving mechanism; and
a stress calculation unit adapted to calculate residual stress of the measuring object based on intensity peaks of the diffracted X-rays detected, respectively, by the first detecting element and the second detecting element each moved by the moving mechanism.
2. The residual stress measuring apparatus according to claim 1, wherein the movement control unit synchronizes movement of the first detecting element and movement of the second detecting element with each other.

3. The residual stress measuring apparatus according to claim 1, wherein the moving mechanism moves the first detecting element and the second detecting element in the same direction.

4. The residual stress measuring apparatus according to claim 1, wherein the moving mechanism moves the first detecting element and the second detecting element by the same distance.

5. The residual stress measuring apparatus according to claim 1, wherein the moving mechanism moves each of the first detecting element and the second detecting element such that a first relative distance between the first detecting element and the position where the X-rays are irradiated and a second relative distance between the second detecting element and the position where the X-rays are irradiated are different.

6. The residual stress measuring apparatus according to claim 1, the first detecting element and the second detecting element are linearly arranged at a predetermined angle with respect to a surface of the measuring object.

7. The residual stress measuring apparatus according to claim 1, wherein the moving mechanism comprises:
 a ball screw portion having a screw shaft;
 an electric motor configured to provide the screw shaft with a turning force around an axial direction; and
 a first nut portion and a second nut portion movably attached to the screw shaft, the first nut portion and the second nut portion movable in the axial direction,
 wherein the first detecting element is attached to the first nut portion and the second detecting element is attached to the second nut portion, and
 wherein the moving mechanism moves each of the first detecting element and the second detecting element along the straight line by driving the electric motor.

8. The residual stress measuring apparatus according to claim 1, wherein the straight line is tilted with respect to a surface of the measuring object.

9. A residual stress measuring method for measuring residual stress of a measuring object using a residual stress measuring apparatus equipped with an X-ray generating source, a first detecting element adapted to detect an intensity of diffracted X-rays of the measuring object at a first detecting position, a second detecting element adapted to detect an intensity of the diffracted X-rays of the measuring object at a second detecting position different from the first detecting position, and a moving mechanism adapted to move each of the first detecting element and the second detecting element along a straight line extending in a direction orthogonal to a direction of incidence of the X-rays, the residual stress measuring method comprising:
 an X-ray irradiation step of radiating X-rays toward the measuring object;
 a movement control step of moving the first detecting element and the second detecting element by driving the moving mechanism, wherein each of the first detecting element and the second detecting element moves such that a relative distance between the respective detecting positions of the first detecting element and the second detecting element and a position where the X-rays are irradiated changes; and
 a stress calculation step of calculating residual stress of the measuring object based on intensity peaks of the diffracted X-rays of the measuring object detected, respectively, by the first detecting element and the second detecting element during execution of the movement control step.

10. The residual stress measuring method according to claim 9, wherein movement of the first detecting element and movement of the second detecting element are synchronized with each other in the movement control step.

11. The residual stress measuring method according to claim 9, wherein the first detecting element and the second detecting element move in the same direction in the movement control step.

12. The residual stress measuring method according to claim 9, wherein the first detecting element and the second detecting element move by the same distance in the movement control step.

13. The residual stress measuring method according to claim 9, wherein each of the first detecting element and the second detecting element moves such that a first relative distance between the first detecting element and the position where the X-rays are irradiated and a second relative distance between the second detecting element and the position where the X-rays are irradiated are different in the movement control step.

14. The residual stress measuring method according to claim 9, the first detecting element and the second detecting element are linearly arranged at a predetermined angle with respect to a surface of the measuring object in the movement control step.

15. The residual stress measuring method according to claim 9, wherein the moving mechanism comprises:
 a ball screw portion having a screw shaft;
 an electric motor configured to provide the screw shaft with a turning force around an axial direction; and
 a first nut portion and a second nut portion movably attached to the screw shaft, the first nut portion and the second nut portion movable in the axial direction,
 wherein the first detecting element is attached to the first nut portion and the second detecting element is attached to the second nut portion, and
 wherein the moving mechanism moves each of the first detecting element and the second detecting element along the straight line by driving the electric motor.

16. The residual stress measuring method according to claim 9, wherein the straight line is tilted with respect to a surface of the measuring object.

* * * * *